(12) United States Patent
Weisblum et al.

(10) Patent No.: US 6,824,994 B2
(45) Date of Patent: Nov. 30, 2004

(54) PEPTIDE LIGANDS THAT MIMIC SENSOR KINASES AND INHIBIT RESPONSE REGULATORS

(75) Inventors: Bernard Weisblum, Madison, WI (US); Andrew T. Ulijasz, Sun Prairie, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 118 days.

(21) Appl. No.: 10/169,658

(22) PCT Filed: Jan. 4, 2001

(86) PCT No.: PCT/US01/00207

§ 371 (c)(1),
(2), (4) Date: Aug. 2, 2002

(87) PCT Pub. No.: WO01/49708

PCT Pub. Date: Jul. 12, 2001

(65) Prior Publication Data

US 2004/0033534 A1 Feb. 19, 2004

Related U.S. Application Data

(60) Provisional application No. 60/174,547, filed on Jan. 5, 2000.

(51) Int. Cl.[7] .......................... A61K 38/00; C07K 4/00
(52) U.S. Cl. .......................... 435/7.2; 514/12; 530/300
(58) Field of Search .......................... 435/7.2; 514/12; 530/300

(56) References Cited

U.S. PATENT DOCUMENTS 6,217,861 B1 * 4/2001 Wallis ........................ 424/94.1

OTHER PUBLICATIONS

G. Wright et al., Purification and Characterization of VanR and the Cytosolic Domain of VanS: A Two–Component Regulatory System Required for Vancomycin Resistance in *Enterococcus faecium* BM4147, 32 Biochem. 5057–5063 (1993).

T. Holman et al., Identification of the DNA–Binding Site for the Phosphorylated VanR Protein Required for Vancomysin Resistance in *Enterococcus faecium* 33 Biochem. 4625–4631 (1994).

S. Fisher et al., Cross–talk between the Histidine Protein Kinase VanS and the Response Regulator PhoB, 270 J. Biol. Chem. 23143–23149 (1995).

A. Haldimann et al., Transcriptional Regulaion of the *Enterococcus faecium* BM4147 Vancomycin Resistance Gene Cluster by the VanS–VanR Two–Component Rgulatory System in *Escherichia coli* K–12, 179 J. Bacteriology 5903–5913 (1997).

A. Ulijasz et al., A Vancomycin–Inducible LacZ Reporter System in *Bacillus subtilis*: Induction by Antibiotics That Inhibit Cell Wall Synthesis and by Lysozyme, 178 J. Bacteriology 6305–6309 (1996).

J. Silva et al., In vivo characterization of the type A and B vancomycin–resistant enterococci (VRE) VanRS two–component systems in *Escherichia coli*: A nonpathogenic model for studying the VRE signal transduction pathways, 95 Proc. Natl. Acad. Sci. USA 11951–11956 (1998).

A. Ulijasz et al., Dissecting the VanRS Signal Transduction Pathway with Specific Inhibitors, 181 J. Bacteriology 627–631 (1999).

R. Novak et al., Emergence of vancomycin tolerance in *Streptococcus pneumoniae*, 399 Nature 590–527 (1999).

J. Hilliard et al., Multiple Mechanisms of Action for Inhibitors of Histidine Protein Kinases from Bacterial Two–Component Systems, 43 Antimicrobial Agents and Chemotherapy 1693–1699 (1999).

A Ulijasz et al., Peptide Analogues of the VanS Catalytic Center Inhibit VanR Binding to Its Cognate Promoter, 39 Biochemistry 11417–11424 (2000).

* cited by examiner

*Primary Examiner*—Karen Cochrane Carlson
*Assistant Examiner*—Anand U Desai
(74) *Attorney, Agent, or Firm*—Quarles & Brady LLP

(57) ABSTRACT

Disclosed herein are methods for exposing a cell to a peptide so as to inhibit binding in a two-component signal transduction system. Such methods can control the development of antibiotic resistance in pathogenic bacteria and other hosts. Peptides useful in such methods, and methods for identifying such peptides, are also disclosed.

5 Claims, No Drawings

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 1

Ser Leu Cys His Asp Ser Val Ile Gly Trp Glu Cys
  1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 2

Ser Leu Ala His Asp Ser Ile Ile Gly Tyr Leu Ser
  1               5                  10

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence:Synthetic
      peptide
```

-continued

```
<400> SEQUENCE: 3

Tyr Leu Ala His Asp Ile Lys Thr Pro Leu Thr Ser Ile Ile Gly Tyr
 1               5                  10                  15
Leu Ser
```

PEPTIDE LIGANDS THAT MIMIC SENSOR KINASES AND INHIBIT RESPONSE REGULATORS

CROSS REFERENCES TO RELATED APPLICATIONS

This is a U.S. application claiming priority on PCT/US01/00207 filed Jan. 4, 2001, which in turn was a continuation in part of U.S. provisional application 60/174,547 filed on Jan. 5, 2000.

STATEMENT REGARDING FEDERALLY SPONSORED RESEARCH OR DEVELOPMENT

This invention was made with United States government support awarded by the following agencies: NIH AI42807. The United States has certain rights in this invention.

REFERENCE TO A SEQUENCE LISTING

A sequence listing referring to three synthetic peptides is attached at the end of this application.

BACKGROUND OF THE INVENTION

The present invention relates to peptides (and methods) for inhibiting two-component signal transduction systems, particularly sensor histidine kinase/cognate receiver aspartyl regulatory protein systems believed responsible for antibiotic resistance developed by certain pathogenic bacteria.

The two-component signal transduction network plays a important role in, among other things, the control of bacterial gene expression, particularly with respect to adaptation to environmental stress. This network includes genes that regulate antibiotic synthesis, antibiotic tolerance (e.g. vancomycin tolerance), toxin production, adaptation to physical stress, xenobiotic metabolism, environmental remediation, phytochrome-based light response, sporulation, motility, quorum sensing, biofilm formation, and virulence.

The proteins which initially mediate the control of these systems, histidine kinases and their cognate aspartyl phosphate response regulators, are also known functionally as "transmitters" and "receivers", respectively. Because such transmitters often sense the environment, they are also referred to as "sensory kinases".

Such "two-component signal transduction systems" are found in bacteria, yeast, fungus and plants. A general discussion of such systems is included in the monograph J. Hoch and T. Silhavy, Two-Component Signal Transduction, ASM Press, Washington, D.C. (1995). See also T. Mizuno, 123 J. Biochem. 555–563 (1998) and M. Pirrung, 6 Chem. Biol. R167–R175 (1999).

A wide variety of such transmitters and receivers have already been identified and cataloged. For example, for 34 bacterial genomes whose sequence determination is completed information relating to these transmitters and receivers is readily available in a specialized database called "SENTRA" (Sensory Transduction Histidine Kinases). The SENTRA web page is funded principally by United States Department of Energy.

The antibiotic resistance two-component systems of initial interest function by autophosphorylation of a transmitter sensor His kinase protein. The phosphoryl moiety is then transferred to an Asp residue of a receiver response regulator protein, symbolically indicated as His→Asp, or H→D. As a consequence of such Asp phosphorylation, the receiver protein shows an increased affinity for a DNA promoter that it binds adjacent to, and thereby activates transcription of the gene(s) that the promoter regulates. In some cases the genes express proteins that ultimately are responsible for antibiotic resistance or tolerance.

The number of such transmitters and receivers in pathogenic bacteria is 26 and 33, respectively, in *E. coli*, but can vary from 6 and 3, respectively, in *Neisseria gonorrhoeae* to 56 and 76, respectively, in *Pseudomonas aeruginosa*. The presence of unequal numbers of receivers and transmitters in a cell indicates that some transmitters or receivers are linked to more than one cognate counterpart.

Three two-component signal transduction systems in *S. pneumoniae* have been identified by name as, ComDe, CiaHR, and VncRS. These systems regulate, respectively, competence for DNA-mediated transformation, resistance to cephotaxime, and vancomycin tolerance. VncRS is of special interest because vancomycin is an important antibiotic of "last resort", and the extent to which bacteria develop tolerance to it diminishes the backup utility of this antibiotic.

VanR and VanS comprise the respective transcriptional response regulator protein and sensor kinase protein of a two-component signal transduction system which regulates vancomycin resistance in *Enterococcus faecium*. See generally A. Haldimann, 179 J. Bacteriol. 5903–5913 (1997). Transcriptional activation of what is known as VanHAXYZ gene cluster is a key event leading to the expression of resistance in induced cells.

VanS, a sensor kinase which is responsive to the presence of vancomycin in the medium, undergoes a net increase in the level of phosphorylation of one of its residues, His-164, by ATP. VanS then transfers the phosphoryl group from His-164 of VanS to Asp-55 of VanR, the response regulator for vancomycin resistance, thereby increasing its affinity for PVanH, the promoter for transcription of the VanHAXYZ gene cluster. VanR~P appears to bind cooperatively as a dimer to the DNA promoter PVanH where it recruits RNA polymerase to initiate transcription of the VanHAXYZ gene cluster. Thus, phosphorylated VanR which is not interfered with leads to greater expression of factors responsible for resistance to the antibiotic.

To date, there has been little success in inhibiting the development of antibiotic resistance in bacteria to certain antibiotics such as vancomycin. Further, the art wishes to develop other means for controlling the development of host cells.

BRIEF SUMMARY OF THE INVENTION

In one aspect the invention provides a method of inhibiting the binding of a phosphorylated receiver aspartyl regulatory protein adjacent a cognate DNA promoter in a host cell. The host cell is selected from the group consisting of bacterial cells (preferably pathogenic bacterial cells such as streptococcus), yeast cells, fungi cells and plant cells, and the host cell is of the type having a two-component signal transduction system. A phosphorylatable receiver aspartyl regulatory protein from which the phosphorylated receiver aspartyl regulatory protein is derived is one component of this system.

In accordance with this method, one exposes the host cell to a peptide of less than two hundred amino acid residues (preferably less than fifty or thirty, even more preferably between six and eighteen residues), the peptide having a histidine residue and having an amino acid sequence portion of at least six amino acid residues which mimic a sensor histidine kinase in the cell that is a second component of the two-component signal transduction system. In this regard, in the absence of the peptide the kinase phosphorylates the phosphorylatable receiver aspartyl regulatory protein.

For purposes of this patent, a peptide is deemed to mimic another amino acid sequence if over a region of at least six amino acid residues of the peptide there is at least 25% (preferably at least 50%, even more preferably at least 66%) homology with respect to a sequence of amino acids of the same length within thirty (preferably within twenty) amino acid residues of a phosphorylation histidine center on the kinase. An even more preferred form of mimicking is if over a region of at least twelve amino acid residues of the peptide there are two such at least six amino acid residue regions of the peptide. One of these regions has at least 50% homology with respect to a first sequence of amino acids of the same length within twenty amino acid residues of the phosphorylation histidine center on the kinase, and another of these regions of the peptide has at least 50% homology with respect to a second sequence of amino acids of the same length within twenty amino acid residues of that phosphorylation histidine center, albeit on an opposite side of the phosphorylation histidine center than the first sequence.

In preferred aspects the host cell is a bacterial cell and the two-component signal transduction system participates in the regulation of the development of resistance of the cell to an antibiotic such as vancomycin. For example, the peptide can be selected from the group consisting of SEQ ID NO. 1 and SEQ ID NO. 2.

In another form the invention provides a method of inhibiting the binding of a receiver aspartyl regulatory protein to a sensor kinase in a host cell. The host cell is again selected from the group consisting of bacterial cells (preferably pathogenic bacterial cells such as streptococcus), fungi, yeast and plant cells, and the host cell has a two-component signal transduction system of which the receiver aspartyl regulatory protein is one component.

In accordance with this method one exposes the host cell to a peptide of less than two hundred amino acid residues (preferably less than fifty or thirty, even more preferably between six and eighteen residues), the peptide having a histidine residue and having a sequence of at least six amino acid residues which mimic a sensor histidine kinase in the cell that is a second component of the two-component signal transduction system. In this regard, in the absence of the peptide the kinase is involved in phosphorylating said receiver aspartyl regulatory protein.

Other preferred forms of this embodiment are peptides capable of reducing the ability of a bacterial cell to tolerate vancomycin. These could be selected from the group consisting of SEQ ID NO. 1 and SEQ ID NO. 2. However, they could also be other peptides that are between six and eighteen amino acid residues in length that mimic the VanS kinase.

Another aspect of the invention provides methods for identifying the above peptides. One approach is, for a selected two-component signal transduction system, to obtain a combinatorial peptide library of peptides of between six and thirty amino acid residues. Preferably, a plurality of peptides in the combinatorial peptide library have a histidine residue and an amino acid sequence portion of at least six amino acid residues which mimics a sensor histidine kinase that is a component of that two-component signal transduction system. One then selects at least one candidate peptide therefrom based on its ability to bind to a receiver aspartyl regulatory protein which is another component of that selected system.

Another approach is, for a selected two-component signal transduction system, to obtain a sequence of a sensor histidine kinase which is one component of the system, and select at least one candidate peptide which mimics that kinase.

It as been surprisingly learned that such two-component signal transduction systems can effectively be inhibited by providing a peptide ligand having less size than the natural kinase that still binds tightly to the receiver regulatory protein, and that the structure of such ligands should preferably closely mimic amino acid sequences adjacent the histidine center of the sensor protein to achieve this. This discovery should be useful across a wide range of pathogenic bacterial cells, other bacterial cells, and other cells that incorporate such two-component systems, albeit particularly with respect to providing a way of inhibiting the ability of bacterial cells to develop resistance to certain antibiotics.

These and other advantages of the present invention will become apparent after study of the following specification and claims.

DETAILED DESCRIPTION OF PREFERRED EMBODIMENTS OF THE INVENTION

Much of the work described herein is reported in greater detail in A. Ulijasz, 39 Biochem. 11417–11424 (2000) (not prior art). The disclosure of this publication is hereby incorporated by reference as if fully set forth herein.

General Overview

The dodecamer peptide, SEQ ID NO. 1, was selected from a combinatorial peptide library on the basis of its ability to bind to VanR, the two-component signal transduction response regulator which controls expression of vancomycin resistance in *Enterococcus faecium*. The binding of this peptide was localized to the N-terminal, regulatory domain of VanR which contains Asp-55, the residue which accepts the phosphoryl group from His-164 in the activated VanS sensor kinase.

SEQ ID NO. 1, along with a related sequence which more closely mimicked the sequence of the VanS kinase, SEQ ID NO. 2, was found to inhibit the binding of VanR~P (the phosphorylated VanR) to a DNA segment which corresponds to its cognate promoter PVanH. With a single gap, both SEQ ID NOS. 1 and 2 could be aligned with the octadecamer sequence SEQ ID NO. 3, comprising Tyr-161 through Ser-178, of the catalytic center dimerization domain of VanS, a sequence with which VanR also normally interacts.

Our findings are that SEQ ID NOS. 1 and 2 mimic the VanS phosphorylatable sequence with which the regulatory domain of VanR interacts, and thus each functions as a "minimalist" analogue of VanS. These results also indicate the usefulness of the techniques we used to identify analogous sequences in other two-component signal transduction response systems. Several examples are provided below of this.

Materials and Methods

Plasmids, bacterial strains, and preferred primers were as described in Table 1 of A. Ulijasz, 39 Biochem. 11417–11424 (2000).

Plasmids and Cloning. Glutathione S-transferase (GST) fusion proteins GST-VanR (complete VanR sequence), GST-VanR regulatory domain (Met-1-Ser-124), GST-DNA binding domain (Ser-123-TAA-231), GST-VanSc (Arg-93-TAA-283 stop), and GST-PhoB (complete PhoB sequence) were constructed in plasmid pGEX-2TK (Amersham Pharmacia Biotech, Piscataway, N.J.) by a modification of procedures described by G. Wright et al., 32 Biochem. 5057–5063 (1993). Four PCR primers were used to prepare each gene cassette by the "melt-anneal" method described previously in A. Ulijasz et al., 178 J. Bacteriol. 6305–6309 (1996).

For each set of four PCR primers, the respective amplimer pairs were denatured, annealed, and ligated. The resultant cassette, with EcoRI and BamHI cohesive ends, was cloned using pGEX-2TK DNA, previously digested with EcoRI and BamHI restriction endonucleases. The unfractionated reaction mixture of ligation products was used to transform Escherichia coli JM109 cells by electroporation, followed by selection for ampicillin resistance. Cells carrying plasmids with inserts were screened by colony PCR. Plasmids specifying the desired fusion constructs were introduced into E. coli BL21 λ DE3 cells for protein over expression.

Over expression and Purification of GST Fusion Proteins. The respective GST fusion proteins were purified on a 1 L scale according to instructions provided by the supplier. The resultant GST-VanR and GST-PhoB proteins were cleaved on the column of glutathione-agarose by incubation with thrombin (2 units) for 4 hours at room temperature, and concentrated by centrifugal ultrafiltration (Centricon 10 concentrator, Amicon, Bedford, Mass.). The resultant VanR preparation, free of GST, was stored in GST elution buffer [50 mM Tris-HCl (pH 7.5), 100 mM NaCl, and 10% glycerol] at –80° C. VanSc-GST was eluted from the column in the same buffer supplemented with 10 mM reduced glutathione, concentrated, stored similarly, and used as the intact GST fusion protein.

Amplification and 5'-End-Labeling of PVanH DNA. A 254 bp DNA fragment containing the PVanH promoter region (residues –191 to 63) was obtained by PCR as described by T. Holman et al., 33 Biochem. 4625–4631 (1994) using a boiled cell preparation of En. faecium A634 as the template source. Amplified PVanH promoter DNA was 5'-end-labeled with [γ-32 P]ATP (specific activity of 200 Ci/mol) and phage T4 polynucleotide kinase. The reaction mixture was incubated for 30 minutes at 37° C., and unincorporated ATP was removed by centrifugal gel filtration (Sephadex G-50 spin column, Amersham Pharmacia Biotech).

Phosphorylation of VanR with Acetyl Phosphate. VanR was phosphorylated as described previously in T. Holman et al., 33 Biochem. 4625–4631 (1994). The reaction was performed in a total volume of 100 µL which contained 50 mM HEPES (pH 7.2), 5 mM $MgCl_2$, 50 mM lithium acetyl phosphate, and 9 µM VanR. After incubation for 1 hour at 37° C., the reaction mixture was used directly as a source of VanR~P, or stored at –80° C. and used within 1 month.

Gel Shift Analysis of VanR ~P Binding to PVanH DNA. VanR-PVanH complexes were quantified by gel shift analysis as described by T. Holman et al., 33 Biochem. 4625–4631 (1994). Complexes were formed in a total volume of 15 µL which contained 4 pmol of VanR-P, which was preincubated with the appropriate effector peptides (as aqueous solutions) for 10 minutes at room temperature in 20 mM HEPES (pH 7.2), 5 mM MgCl2, 0.1 mM $Na_2$EDTA, 0.5 mM $CaCl_2$, 10% glycerol, and 0.5 µg of salmon sperm DNA.

To start the reaction, $^{32}$P-labeled PVanH promoter probe DNA (0.65 ng in 1 µL) was added, and the reaction mixture was incubated on ice for 15 minutes. The resultant VanR~P-PVanH complexes were analyzed by nondenaturing PAGE. See generally J. Sambrook et al., Molecular Cloning: A Laboratory Manual, 2nd Ed. (1989). Gels were cast in TAE buffer, and electrophoresis was performed in the same buffer at 155 V for 45 minutes. Gels were then dried on Whatman® 3MM filter paper, and exposed to a phosphorimager screen overnight for analysis of DNA-protein complexes.

Phosphotransferase Assay. VanSc-GST (4 pmol) was labeled for 60 minutes at room temperature in a 5 µL volume containing, 50 mM Tris-HCl (pH 7.4), 5 mM $MgCl_2$, and 100 mM KCl. The reaction was initiated by addition of 1 µL of 200 µM [γ-$^{32}$P]ATP which contained 1 µCi. After 60 minutes, the 5 µL reaction mixture was added to a 15 µL reaction mixture containing 80 pmol of PhoB and 2.5 mM PMSF all in the same buffer, with the appropriate peptide at a final concentration of 1 mM. Reactions were stopped by the addition of 10 µL of SDS gel loading buffer, and the resultant mixture was fractionated by SDS-PAGE. Phosphoproteins were assessed autoradiographically with a phosphorimager, as previously described.

Phage Display. Phage display was performed using the methods described by A. Sparks et al., Phage Display Of Peptides And Proteins; A Laboratory Manual (1996). Microtiter plate wells were coated with purified VanR and used to select binding phage from a library displaying combinatorial peptides, i.e., 10 random NNK codons followed by a Cys codon, TGC, in the eleventh position (N is A, G, C, or T, and K is G or T). After three rounds of selection, the binding of individual phage clones to the VanR target protein was assessed by phage-ELISA using an anti-M13 phage monoclonal antibody-horseradish peroxidase conjugate (Pharmacia). Ninety-six phage plaques were picked from the third round of selection and tested for their ability to bind to VanR and to BSA, by phage ELISA, to determine levels of specific and background binding, respectively.

For inserting determinants for desired peptide sequences into phage M13 DNA, oligonucleotides encoding the defined peptide sequences were cloned into the XhoI and XbaI sites within gene III of bacteriophage M13. The resulting recombinant phage were then tested for binding to various protein targets, immobilized within microtiter plate wells, by phage ELISA. A. Sparks et al., Phage Display Of Peptides And Proteins; A Laboratory Manual (1996).

Sequence Analysis of Combinatorial Peptides. Of the 96 chosen phage plaques, 25 isolates with a relative selectivity for VanR relative to BSA greater than a factor of 4 (by phage ELISA) were selected for DNA sequence analysis. The deduced peptide sequences were further analyzed by alignment with the amino acid sequence of VanS using the program MultAlin. F. Corpet, 16 Nuc. Acid. Res., 10881–10890 (1988).

Chemical Synthesis of Combinatorial Peptides. Peptides were chemically synthesized by Chiron Technologies (Raleigh, N.C.) and Research Genetics (Huntsville, Ala.). They were purified by the supplier using HPLC, and further analyzed by mass spectrometry.

Construction of Alanine Substitution Mutants of VanSc. Alanine substitutions were incorporated into the VanS soluble intracellular domain construct, GST-VanSc, by overlap-extension PCR. R. Horton et al., 217 Methods Enzymol. 270–279 (1993). Two paired sets of primers were used for each mutant construction. The first pair consisted of a 5'-forward primer encoding the N-terminus of the VanSc construct and a counterpart reverse primer, which encoded the alanine-substituted SEQ ID NO. 1 peptide homologue.

The second pair consisted of a 5'-forward primer encoding the complementary alanine-substituted SEQ ID NO. 1 peptide homologue and a counterpart reverse primer, which encoded the C-terminus of VanSc. The two resultant amplimers were gel-purified, denatured, annealed, and extended with Pfu DNA polymerase. The full-length construct was then amplified using the forward and reverse VanSc primers. The resultant amplimer was cloned in plasmid pGEX-2TK for high-level expression in E. coli. The resultant mutant construct was overexpressed as a GST fusion protein and purified for binding experiments.

Results of SEQ ID NOS. 1 and 2 Experiments

Screening for Peptides Which Bind to VanR. Microtiter plate wells, coated with purified VanR, were used to select peptides from a phage library displaying combinatorial peptides on capsid protein III. After three rounds of screening and amplification of the library, 96 phage plaques were chosen for further characterization by phage ELISA. Of these, 20 phage exhibited ≧4-fold more binding to VanR than to BSA, i.e., an unrelated target. These phage were selected for DNA sequencing and determination of the amino acid sequences of their respective inserts. Further details regarding these experiments are described in Table 2 of A. Ulijasz, 39 Biochem. 11417–11424 (2000). One of the peptide sequences, SEQ ID NO. 1, occurred 6 out of 25 times and bound reproducibly to the cloned regulatory domain of VanR preferentially.

Effect of Peptide E12 on VanR~PVanH Complex Formation. Peptide SEQ ID NO. 1 was chemically synthesized in the disulfide form and tested for its ability to inhibit the interaction between a $^{32}$P-labeled DNA segment of the PVanH promoter and VanR. Results indicated that SEQ ID NO. 1 inhibited the interaction between VanR and PVanH.

Similarity between SEQ ID NO. 1 and the Catalytic Center of VanS. When we used the program MultAlin to compare SEQ ID NO. 1 with VanS, we found a match with the 18-amino acid sequence, residues Tyr-161-Ser-178, by introducing a six-amino acid gap in SEQ ID NO. 1. This match suggested that SEQ ID NO. 1 was acting as an analogue of the VanS sequence Tyr-161-Ser-178. SEQ ID NO. 1 was therefore used as a lead peptide to design and test whether more precise peptide mimics of the VanS catalytic center might be more effective at inhibiting the binding of VanR to PVanH.

A modified peptide, SEQ ID NO. 2 which more closely resembled the sequence of VanS. Peptide SEQ ID NO. 2 incorporated a pentapeptide sequence and another heptapeptide sequence of VanS, but not the central six residues. In addition, the two Cys residues of SEQ ID NO. 1 were replaced with Ala and Ser, simplifying the synthesis of Ala-substituted variant peptides used in later experiments. The Ser residue which corresponds to Tyr-161 was derived from the sequence of M13.

In testing SEQ ID NO. 2, we compared its activity with that of SEQ ID NO. 1 under conditions which utilize the physiologically active form of VanR, VanR~P, as well. In comparing SEQ ID NO. 1 binding to VanR with binding to VanR~P, we found a >100-fold difference. SEQ ID NO. 2 was tested for its ability to inhibit VanR~P-[$^{32}$P] PVanH complex formation as the target. The results indicate that the IC$_{50}$ for peptide SEQ ID NO. 2 was a >10-fold increase over that of SEQ ID NO. 1 for inhibiting VanR~P binding to [$^{32}$P] PVanH. See generally C. Fabret et al., 180 J. Bacteriol. 6375–6383 (1990); S. Fisher et al., 270 J. Biol. Chem. 23143–23149 (1995), suggesting that the closer similarity was responsible for tighter binding in SEQ ID NO. 2.

Alanine Substitution Analysis of Peptide SEQ ID NO. 2 with Respect to VanR~P-PVanH Complex Formation. We next tested the hypothesis that the inhibitory activity of SEQ ID NO. 2 toward VanR~P-PVanH complex formation may be due to its resemblance to VanS by evaluating the contribution of the residues within SEQ ID NO. 2 toward inhibiting the interaction between VanR~P and PVanH DNA. A set of 12 individual Ala-substituted variants of E12.1 were chemically synthesized and tested.

The results listed in Table 3 of A. Ulijasz, 39 Biochem. 11417–11424 (2000), indicate that of the 12 alanine-substituted peptides, six inhibited the VanR~P-induced mobility shift of the PVanH DNA probe. These observations indicate that for at least five of 11 substituted peptides that were tested, the amino acid could be replaced with Ala without a loss of activity, suggesting that these amino acids were not as critical for inhibitory activity.

Specificity of Chemically Synthesized SEQ ID NO. 2 E12.1 as an Inhibitor of Phosphoryl Transfer from P~VanS to PhoB. We now demonstrate that peptide SEQ ID NO. 2 can also inhibit phosphoryl transfer. Since the affinity of VanS for VanR is in the nanomolar range, we used a weakened but nevertheless specific interaction, namely, between VanS and PhoB. VanS~P was incubated with PhoB, and phosphoryl transfer was assessed. The results indicate that 1 mM SEQ ID NO. 2 inhibited phosphoryl transfer.

Other Experiments

We then confirmed that short peptide fragments (e.g. 18-mer amino acid sequences) of other transmitter kinases centering around their histidine phosphorylation centers can bind specifically to their cognate response regulators. For example, we constructed phages which display the predicted kinase sequences (based on known sequence data) by insertion of the respective DNA cassette into mBAX phagemid DNA. A. Sparks et al., Phage Display Of Peptides And Proteins; A Laboratory Manual (1996). The surface protein pIII specified by mBAX is unsubstituted, and its gene contains a multiple cloning site (XhoI-XbaI) into which peptide-determinant cassettes can be inserted for surface display. The phage library used earlier in this work was constructed by insertion of a combinatorial sequence into this same site.

In particular, two additional transmitter kinase sequences from Streptococcus (PhoR with respect to PhoB; and EnvZ with respect to OmpR), and their respective cassettes were tried. The respective cassettes were ligated to mBAX DNA digested with XhoI and XbaI restriction endonucleases. The resultant ligation reaction was transfected into E. coli DH5αF'.

Phage plaques were picked and the nucleotide sequence of the insert was determined and verified. Phase lysates were prepared and verified. Phage lysates were prepared and tested by phase ELISA with the respective response regulators bound to the microtiter plate wells. Results of the ELISA indicate that each phage binds to its expected target and less so to a GST blank.

This work would indicate that the regions around the histidine centers in the sensor kinases can be mimicked to create corresponding minimalist binding peptides. If desired, the peptide can be created without several residues on each side of the histidine center amino acid, but with mimicking sections corresponding to opposing portions on each side of that region.

One possible use of the present invention is to add the peptides of the present invention into a culture broth so as to better selectively suppress the tendency of bacteria (which may be a contaminant in the broth) to grow resistance to a suppressing antibiotic in the broth (while permitting growth of something that is added that is not suppressed by the suppressing antibiotic). For example, vancomycin can suppress *Streptococcus pneumoniae*, and that bacteria has a tendency to accept through its cell wall small peptides (e.g. in the 17 mer range).

Alternatively, the inhibitory peptide could be fused to another peptide such as a competence-stimulating peptide (CSP) that the bacteria readily accepts through its cell wall. See e.g. L. Havarstein et al., 92 P.N.A.S. USA 11140–11144 (1995). The fusion peptide can then be included in the culture media.

Another potential use would be to deliver the peptide to a living mammal along with the antibiotic. Presumably, DNA coding for the peptide could be inserted in an expression vector and then delivered to the body. Other administration techniques could be used as well (e.g. delivery of the peptide directly).

The invention also has significant research value in helping researchers analyze the purpose and function of various genes and proteins. Signal transduction might also provide a useful target at which to aim for the discovery of new classes of anti-infective agents when this mechanism is involved in the infection process.

Several classes of kinase inhibitors that are active in vitro have already been described as noted in A. Ulijasz et al., 39 Biochem. 11417–11424 (2000). However, complete inhibition of any one kinase may be circumvented by cross-talk with noncognate kinases. Moreover, there have been reports that some agents reported to inhibit His kinases also inhibited either membrane integrity, uridine, or amino acid incorporation, at comparable concentrations, and therefore were not as selective as was originally thought.

The response regulator is therefore a more suitable target. The example of VanR-VanS is instructive. It was demonstrated that mutational inactivation of VanS could actually lead to vancomycin tolerance in clinical isolates of *Streptococcus pneumoniae*. In this case, genetic ablation of kinase function actually provoked cells to become tolerant of vancomycin. The inactivation of *S. pneumoniae* VncR by site-specific recombination-mediated gene disruption was actually lethal.

While the above experiments focus on pathogenic bacteria, and in particular two-component regulatory systems that relate to antibiotic resistance control, the invention is not so limited. Rather, the invention is intended to provide general techniques for inhibiting such systems by identifying and using peptides that mimic the sensor kinase component.

Thus, the claims should be looked to in order to judge the full scope of the invention.

INDUSTRIAL APPLICABILITY

The present invention provides inhibitor peptides useful to suppress the development of antibiotic resistance in bacteria.

We claim:

1. A method of inhibiting the binding of VanR receiver aspartyl regulatory protein to VanS sensor kinase in a bacterial cell, the bacterial cell having a two-component signal transduction system which participates in the regulation of the development of resistance of the cell to an antibiotic and of which the VanR receiver aspartyl regulatory protein is one component, the method comprising:

exposing the bacterial cell to a peptide of less than two hundred amino acid residues, the peptide having a histidine residue and having an amino acid sequence portion of at least six amino acid residues which mimics an amino acid sequence of VanS sensor histidine kinase in the cell that is a second component of the two-component signal transduction system in that in the absence of the peptide the kinase is involved in phosphorylating the phosphorylatable VanR receiver aspartyl regulatory protein.

2. A method of inhibiting the binding of a receiver aspartyl regulatory protein to a sensor kinase in a bacterial cell, the bacterial cell having a two-component signal transduction system which participates in the regulation of the development of resistance of the cell to an antibiotic and of which the receiver aspartyl regulatory protein is one component, the method comprising:

exposing the bacterial cell to a peptide of less than two hundred amino acid residues, the peptide having a histidine residue and having an amino acid sequence portion of at least six amino acid residues which mimics an amino acid sequence of a sensor histidine kinase in the cell that is a second component of the two-component signal transduction system in that in the absence of the peptide the kinase is involved in phosphorylating the phosphorylatable receiver aspartyl regulatory protein;

wherein the peptide is between six and thirty amino acids in length.

3. The method of claim 2, wherein the antibiotic is vancomycin.

4. The method of claim 3, wherein the peptide is selected from the group consisting of SEQ ID NO. 1 and SEQ ID NO. 2.

5. A peptide capable of reducing the ability of a bacterial cell to tolerate vancomycin, comprising a peptide selected from the group consisting of SEQ ID NO. 1 and SEQ ID No. 2.

* * * * *